United States Patent
Olson

(10) Patent No.: US 10,271,794 B2
(45) Date of Patent: Apr. 30, 2019

(54) SYSTEM AND METHOD FOR RENDERING A MOTION MODEL OF A BEATING HEART

(71) Applicant: St. Jude Medical, Cardiology Division, Inc., St. Paul, MN (US)

(72) Inventor: Eric S. Olson, Maplewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 229 days.

(21) Appl. No.: 15/118,520

(22) PCT Filed: Apr. 29, 2015

(86) PCT No.: PCT/US2015/028206
§ 371 (c)(1),
(2) Date: Aug. 12, 2016

(87) PCT Pub. No.: WO2015/171393
PCT Pub. Date: Nov. 12, 2015

(65) Prior Publication Data
US 2017/0042481 A1 Feb. 16, 2017

Related U.S. Application Data

(60) Provisional application No. 61/988,553, filed on May 5, 2014.

(51) Int. Cl.
*A61B 5/04* (2006.01)
*A61B 5/00* (2006.01)
(Continued)

(52) U.S. Cl.
CPC .......... *A61B 5/6852* (2013.01); *A61B 5/0422* (2013.01); *A61B 5/0452* (2013.01);
(Continued)

(58) Field of Classification Search
CPC ............................ A61B 5/6852; A61B 5/7285
See application file for complete search history.

(56) References Cited

U.S. PATENT DOCUMENTS 6,633,686 B1  10/2003  Bakircioglu et al.
7,263,397 B2   8/2007  Hauck et al.
(Continued)

FOREIGN PATENT DOCUMENTS

CN    101283908 A   10/2008
EP      2121099 A2   11/2009
(Continued)

OTHER PUBLICATIONS

Chesnokov, D., Individually adaptable Automatic QT Detector, Computers in Cardiology, 2006, 33:337-341.
(Continued)

*Primary Examiner* — Eric D. Bertram
(74) *Attorney, Agent, or Firm* — Dykema Gossett PLLC

(57) ABSTRACT

Location data associated with a cardiac wall motion during a cardiac cycle can be received. The cardiac cycle can be divided into incremental phases. The location data associated with the cardiac wall motion can be assigned to the incremental phases. A fiducial pair of coordinates can be determined for each of the incremental phases. The fiducial pair of coordinates can include location data for an intermediate cardiac phase and location data for a reference cardiac phase. A fiducial loop can be determined from the fiducial pair of coordinates for each of the incremental phases. A learned cardiac mapping between the reference cardiac phase and the intermediate cardiac phase can be determined using the fiducial loop.

20 Claims, 6 Drawing Sheets

(51) Int. Cl.

| | |
|---|---|
| G16H 50/50 | (2018.01) |
| A61B 5/042 | (2006.01) |
| A61B 5/0452 | (2006.01) |
| A61B 5/06 | (2006.01) |
| A61B 5/11 | (2006.01) |
| G06T 13/40 | (2011.01) |
| G06T 19/00 | (2011.01) |
| G06T 15/04 | (2011.01) |
| G06F 19/00 | (2018.01) |

(52) U.S. Cl.
CPC .............. *A61B 5/06* (2013.01); *A61B 5/1107* (2013.01); *A61B 5/6869* (2013.01); *A61B 5/7285* (2013.01); *A61B 5/742* (2013.01); *G06F 19/00* (2013.01); *G06T 13/40* (2013.01); *G06T 15/04* (2013.01); *G06T 19/00* (2013.01); *G16H 50/50* (2018.01); *A61B 5/062* (2013.01); *A61B 5/063* (2013.01); *G06T 2207/10072* (2013.01); *G06T 2207/30048* (2013.01); *G06T 2210/41* (2013.01); *G06T 2210/56* (2013.01)

(56) References Cited

U.S. PATENT DOCUMENTS

| | | | |
|---|---|---|---|
| 2003/0093067 A1* | 5/2003 | Panescu | A61B 5/0422 606/32 |
| 2003/0233039 A1 | 12/2003 | Shao et al. | |
| 2008/0221439 A1* | 9/2008 | Iddan | A61B 6/12 600/424 |
| 2009/0275828 A1 | 11/2009 | Shachar et al. | |
| 2010/0168550 A1 | 7/2010 | Byrd et al. | |
| 2012/0184863 A1 | 7/2012 | Harley et al. | |
| 2012/0277567 A1 | 11/2012 | Harlev et al. | |
| 2013/0079626 A1* | 3/2013 | Shmatukha | A61B 6/03 600/420 |
| 2013/0222415 A1 | 8/2013 | Vilsmeier | |
| 2015/0313510 A1 | 11/2015 | Razavi et al. | |

FOREIGN PATENT DOCUMENTS

| | | |
|---|---|---|
| EP | 2757528 A1 | 7/2014 |
| JP | 2001061789 A | 3/2001 |
| JP | 2006511296 A | 4/2006 |
| WO | 2004060158 A1 | 7/2004 |

OTHER PUBLICATIONS

Bookstein, F.L., Principal Warps: Thin Plate Splines and the Decomposition of Deformations, IEEE Transactions on Pattern Analysis and Machine Intelligence, 1989, 11:567-585. Proceedings of the 12th International Conference on Information Processing in Medical Imaging, Jul. 1991.

Segars, Paul W. et al., A Realistic Spline-Based Dynamic Heart Phantom, IEEE Transactions on Nuclear Science, IEEE Service Center, New York, NY, vol. 46, No. 3, Jun. 1, 1999; pp. 503-506.

Quatember, E., et al., Geometric modeling and motion analysis of the epicardial surface of the heart, Mathematics and Computers in Simulation, vol. 81, No. 3, Nov. 1, 2010, pp. 608-622.

Bogatyrenko, Evgeniya, et al., Efficient physics-based tracking of heart surface motion for beating heart surgery robotic systems, International Journal of Computer Assisted Radiology and Surgery, vol. 6, No. 3, Aug. 6, 2010, pp. 387-399.

Bbokstein, F. L. Thin-Plate Splines and the Atlas Problem for Biomedical Images. Proceedings of the 12th International Conference on Information Processing in Medical Imaging, Springer, Jul. 1991, p. 326-342.

CN Search Report dated Jul. 26, 2018 (2 pages).

First Notice of Reason for Rejection (JP Office action dated Dec. 5, 2017); extracted p. 2 (1 page).

* cited by examiner

SYSTEM AND METHOD FOR RENDERING A MOTION MODEL OF A BEATING HEART

CROSS-REFERENCE TO RELATED APPLICATION

This application claims priority to U.S. provisional patent application No. 61/988,553 entitled "SYSTEM AND METHOD FOR RENDERING A MOTION MODEL OF A BEATING HEART", filed 5 May 2014. This application is also related to U.S. application Ser. No. 14/270,176 entitled "METHOD AND SYSTEM FOR DISPLAYING A THREE DIMENSIONAL VISUALIZATION OF CARDIAC MOTION", filed 5 May 2014.

BACKGROUND a. Field of the Disclosure

This disclosure relates to a determination of a cardiac mapping, and in particular, rendering a motion model of a beating heart.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature and to the intended site, for example, a site within the patient's heart, and carries one or more electrodes, which may be used for mapping, ablation, diagnosis, or other treatments.

A variety of techniques have been employed to provide a rendering of the heart or chambers of the heart using the mapping data received by the one or more electrodes carried by the catheter. For instance, it is known to provide a catheter navigation and mapping system, as set forth in U.S. Pat. No. 7,263,397 issued to Hauck et al., hereby incorporated by reference as though fully set forth herein. Hauck et al. generally discloses a medical system for finding and displaying the location of electrodes within the body. Hauck et al. further disclose that a roving electrode is swept throughout the heart chamber while the heart is beating, and a large number of electrode locations (e.g., data points) are received. Such data points are taken at all stages of the heart beat and without regard to the cardiac phase. Since the heart changes shape during contraction, only a small number of the points represent the maximum heart volume. Moreover, Hauck et al. teaches selecting the most exterior points to create a shell that represents the shape (e.g., geometry, volume) of the heart, or chamber thereof, at its maximum size. Once the shell is constructed, received EP data may be subsequently mapped onto the shell and displayed to a user.

Byrd et al. (U.S. patent application Ser. No. 12/347,216, filed Dec. 31, 2008), hereby incorporated by reference as though fully set forth herein, collects a plurality of sensor locations (e.g., data points) by a localization system, including a respective indication of the cardiac phase during, or at which, each point was acquired. Shells are constructed from these data points, which may be played back as per a patient's real-time measured electrocardiogram (ECG) to generate a respective geometry of the heart chamber during a particular cardiac phase specified for each point, or set of points.

SUMMARY

In various embodiments, a method is provided for rendering a motion model of a heart. The method can include receiving location data associated with a cardiac wall motion during a cardiac cycle. The cardiac cycle can be divided into incremental phases, and the location data associated with the cardiac wall motion can be assigned to the incremental phases. The method can include determining a fiducial pair of coordinates for each of the incremental phases. In some embodiments, the fiducial pair of coordinates includes location data for an intermediate cardiac phase and location data for a reference cardiac phase. In some embodiments, the learned cardiac mapping between the reference cardiac phase and the intermediate cardiac phase can include computing a geometry of the heart for at least one incremental phase. The method can include constructing a fiducial loop from the fiducial pair of coordinates for each of the incremental phases. The method can include determining a learned cardiac mapping between the reference cardiac phase and the intermediate cardiac phase using the fiducial loop. Determining the learned cardiac mapping between the reference cardiac phase and the intermediate cardiac phase can include computing a lookup table of phase geometries. In some embodiments, the method can include receiving a surface model of the heart that corresponds to the reference cardiac phase. A coordinate associated with the surface model of the heart can be shifted using the lookup table of phase geometries. Shifting the coordinate associated with the surface model of the heart can be determined by correlating a cardiac phase with a phase geometry in the table of phase geometries. In some embodiments, the method can include determining a current cardiac mapping using the learned cardiac mapping and a current cardiac phase. In some embodiments, the current cardiac phase can be determined based on a previous cardiac phase. For example, the current cardiac phase can be determined based on a ratio between a time associated with a length of the previous cardiac cycle and a time since a current cardiac cycle began.

In various embodiments, instructions are executable by a processing resource for rendering a motion model of a heart. A surface model of the heart corresponding to an end diastole portion of the cardiac cycle can be received. Location data associated with a cardiac wall motion during the cardiac cycle can be received. In some embodiments, the location data associated with the cardiac wall motion can be received from a sensor inserted into the heart. In some embodiments, the cardiac cycle can be divided into incremental phases. The location data associated with the cardiac wall motion can be assigned to the incremental phases based on a corresponding cardiac phase associated with the location data. In some embodiments, an average of the location data assigned to each of the incremental phases can be determined. A fiducial pair of coordinates can be determined for each of the incremental phases from the averaged location data. The fiducial pair of coordinates can be interpolated in response to the current cardiac phase being between adjacent incremental phases. A fiducial loop can be constructed from the fiducial pair of coordinates for each of the incremental phases. In some embodiments, a lookup table of phase geometries can be computed based on the fiducial loop and a shift in coordinates of the surface model can be determined based on the lookup table and a current cardiac phase of the cardiac cycle. In some embodiments, the fiducial pair of coordinates can be an offset from a coordinate associated with the surface model of the heart. In some embodiments, the fiducial pair of coordinates can be an absolute location of the coordinate associated with the surface model of the heart. In some embodiments, a geometry of the heart can be displayed based on the current cardiac phase of the cardiac cycle using the lookup table. An animation of a change in the geometry of the heart can be displayed during the cardiac cycle based on the current cardiac phase of the cardiac cycle using the lookup table.

In various embodiments, a system for rendering a motion model of a heart is provided to receive a motion sample associated with a cardiac wall motion during a cardiac cycle from a sensor operatively connected to a catheter. The motion sample can contain location data associated with the cardiac wall motion and a cardiac phase associated with the location data. In some embodiments, the cardiac cycle can be divided into incremental phases and location data can be assigned to the incremental phases based on the corresponding cardiac phase data. A fiducial pair of coordinates can be determined for each of the incremental phases based on the assigned location data and a fiducial loop can be constructed from the fiducial pair of coordinates for each of the incremental phases. The fiducial pair of coordinates can include location data for an intermediate cardiac phase and location data for an end cardiac phase. In some embodiments, a learned cardiac mapping for the cardiac cycle can be determined and can include a lookup table of phase geometries. An animation of a current cardiac cycle can be displayed based on the lookup table of phase geometries and a current cardiac phase. In some embodiments, a surface model of a heart corresponding to the end cardiac phase can be received. A coordinate of the surface model can be shifted through use of the lookup table of phase geometries and the current cardiac phase. In an example, the animation of the current cardiac cycle can be provided by shifting the coordinate of the surface model over each incremental phase of the cardiac cycle.

DETAILED DESCRIPTION

Figure 1:
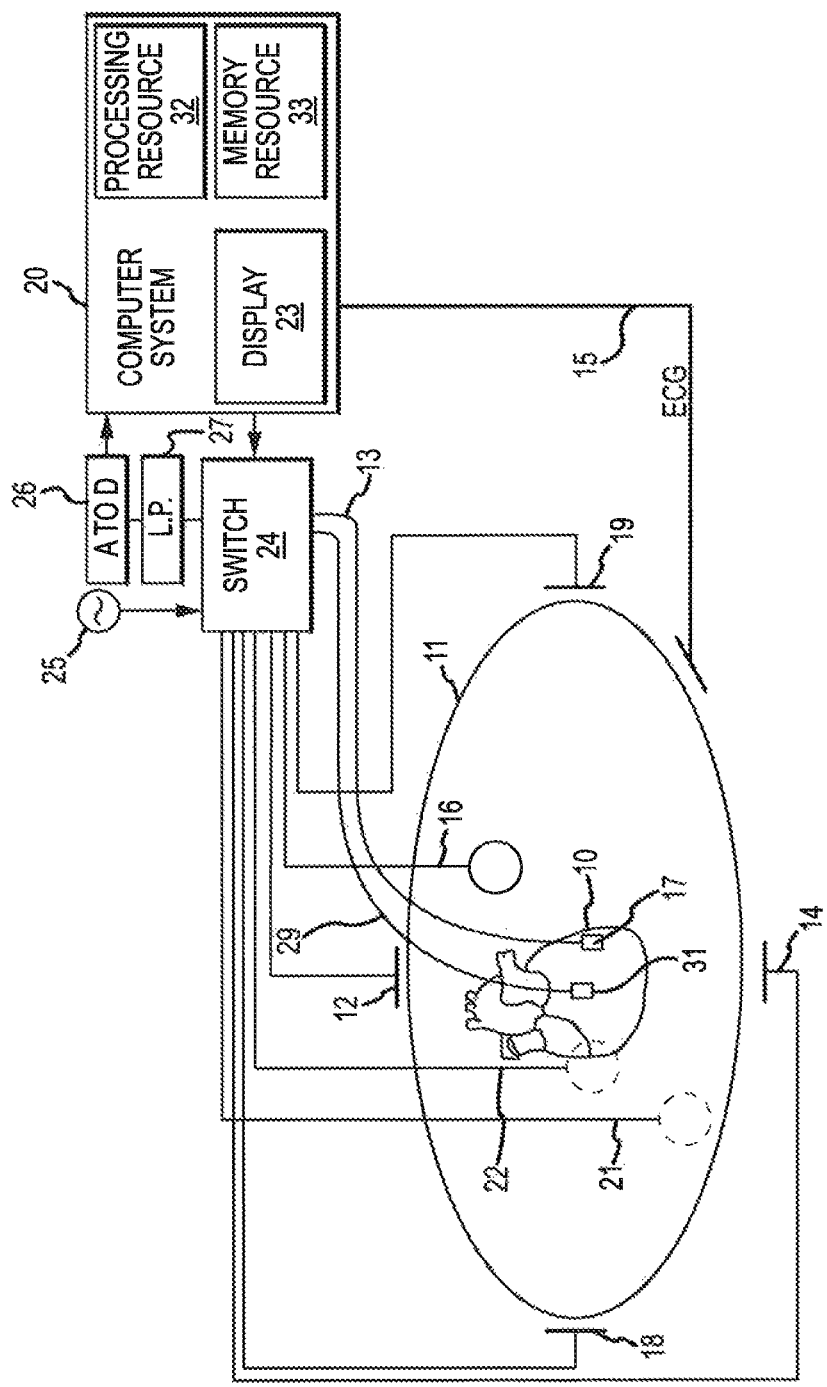
FIG. 1 illustrates a system for rendering a motion model of a heart, in accordance with embodiments of the present disclosure.

Referring now to the drawings wherein like reference numerals are used to identify identical components in the various views, FIG. 1 is a diagrammatic overview of a catheter system in which the invention may be practiced. The system may comprise various visualization, mapping and navigation components as known in the art, including among others, for example, an EnSite™ Velocity™ Cardiac Mapping and Visualization System commercially available from St. Jude Medical, Inc., or as seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. In addition, the system may include components, as seen generally by reference to U.S. application Ser. No. 14/270,176 entitled "METHOD AND SYSTEM FOR DISPLAYING A THREE DIMENSIONAL VISUALIZATION OF CARDIAC MOTION", filed 5 May 2014, owned by the common assignee of the present invention, and hereby incorporated by reference in its entirety. The system may be used in connection with or for various medical procedures, for example, mapping of the heart and/or cardiac ablation procedures. Although reference is made to cardiac mapping of the heart, one or more aspects of the present disclosure may apply to other anatomic structures. It should be understood that embodiments consistent with the invention may, and typically will, include other features not shown or described herein for the sake of brevity and clarity. For example, when used in connection with an ablation catheter, such an ablation catheter may typically include various electrodes and corresponding leads; a temperature sensor and corresponding leads; and other features as known in the art.

Some imaging systems can capture 4-dimensional image data and can replay the image data in sequence in order to provide cinematographic loops. These moving images can provide an ability to visualize the beating heart. In contrast to the embodiments disclosed herein, 4-dimensional cinematographic loops can be based on image data collected over time, whereas embodiments of the present disclosure can be based on a motion captured via a roving catheter as measured by an electrophysiology localization system such as the EnSite™ Velocity™ system. Additionally, 4-dimensional cinematographic loops can be based on the replay of image data whereas embodiments of the present disclosure are based on the animation of surface models in a 3-dimensional rendering environment, such as OpenGL™ or DirectX™.

As described in the Background, some visualization/navigation systems use a single, static shell to represent the surface geometry and size/volume of the heart, or chamber thereof. One conventional approach to construct such a shell is to use the collected electrode locations that correspond to the largest volume of the heart chamber being modeled.

In an example, Byrd et al. (U.S. patent application Ser. No. 12/347,216, filed Dec. 31, 2008), relies on collecting a cloud of points via a roving catheter in an electrophysiology mapping system. The cloud of points are sorted and binned based on the associated cardiac phase. Multiple geometries can be reconstructed from each set of binned geometry points and used to create multiple surface models. The mapping system determines the cardiac phase from an electrocardiogram (ECG) and displays the appropriate geometry according to the determined cardiac phase. However, certain regions within the heart may not contain points sampled over all cardiac phases, which can lead to a reconstructed geometry that is not representative of an actual physical motion of the heart. As such, a portion of the heart may appear to move in a particular location when particular geometries are displayed in succession to create the animation of cardiac motion. However, the portion of the heart may appear to move not because the cardiac wall (e.g., endocardial, epicardial wall) is moving, but because a region was under-sampled.

In addition, interpolating between geometries reconstructed from differing sets of binned point clouds can prove difficult because each such geometry can have a different mesh topology. Interpolation between such topologies can be a difficult task. Each mesh topology can have a different number of facets/triangles. As such, adding/removing the triangles would be required in order to interpolate/transition between these geometries, which can be more computationally intensive than embodiments provided by the present disclosure.

Embodiments of the present disclosure can use a single geometry to create a surface model and can morph a geometry (e.g., having identical topologies) of the surface model (e.g., shift coordinates associated with the surface model) to form a particular geometry associated with various cardiac phases of the heart and develop a learned cardiac mapping for use in rendering a motion model of a beating heart. As used herein, a learned cardiac mapping can include a mapping of a particular geometry of the heart associated with a particular cardiac phase and/or time period. Since a single geometry is used to create the surface model, reconstruction of multiple geometries that may not be representative of the actual physical motion of the heart can be avoided.

In some examples, function regression (e.g., thin plate splines model) can be used to map points on a statically collected surface model representing a heart chamber to differing points based on where a particular location of the heart is located at different cardiac phases. For example, a point cloud collected over all cardiac phases can represent an end diastolic geometry. By placing a catheter at a particular location on a surface of the heart (e.g., cardiac wall), and observing its position at different cardiac phases, such as systole, a fiducial point can be collected that represents the offset of the surface location from diastole to systole. In some embodiments, this can be performed for more than diastole and systole. For example, fiducial points can be collected that represent multiple cardiac phases, such as every 10% phase.

Referring again to FIG. 1, the catheter system includes a diagrammatic depiction of a heart 10 of a patient 11. The system includes the ability to receive a plurality of catheter locations as the catheter distal end is swept around and within a chamber of the heart. For this purpose, FIG. 1 shows an exemplary catheter localization system of the type based on externally-applied orthogonal electric fields which are used to determine the location of one or more catheter electrodes. Such a system is known generally in the art (e.g., an EnSite NAVX™ Navigation and Visualization System). It should be understood, however, that this embodiment is exemplary only and not limiting in nature. Other technologies for determining the location in 3D space of a catheter, such as the MediGuide™ system, may be used in practicing the present invention, including, for example, the CARTO navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more electrodes, for example, in the case of an impedance-based localization system. In some embodiments, the sensor may include one or more coils (e.g., wire windings) configured to detect one or more characteristics of a magnetic field, for example, in the case of a magnetic-field based localization system.

It should be further understood that in some localization systems, one or more electrodes may collectively define the sensor. The one or more electrodes may be provided on a distal end of a catheter and the localization system may be configured to obtain location information from the one or more of the electrodes. The localization system may compute a distal location of the catheter using not only the received location information, but also a geometrical relationship between the one or more electrodes providing the location information and the distal location on the catheter (e.g., one piece of geometrical information may be the ring electrode to tip distance). Finally, the localization system may use the computed location, as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1, in the illustrated impedance-based localization system embodiment, three sets of surface electrodes (e.g., applied via a patch) are shown: X-axis electrodes 12, 14; Y-axis electrodes 18, 19; and Z-axis electrodes 16, 22. Additionally, an additional surface electrode 21 (e.g., applied via a "belly" patch) may be used. The surface electrodes are all connected to a switch 24. A representative catheter 13 is shown, which has a single distal electrode 17, which may be referred to herein as a "roving" or "measurement" electrode. The electrode 17 may define the location sensor in this embodiment, but as alluded to above, many variations are possible. FIG. 1 also shows a second, independent catheter 29 with a fixed reference electrode 31, which may be stationary on the heart 10 far calibration purposes.

FIG. 1 further shows a computer system 20, a signal generator 25, an analog-to-digital converter 26 and a low-pass filter 27. The computer system 20 can utilize software, hardware, firmware, and/or logic to perform a number of functions described herein. The computing system 20 can be a combination of hardware and instructions to share information. The hardware, for example can include processing resource 32 and/or a memory resource 33 (e.g., non-transitory computer-readable medium (CRM) database, etc.). A processing resource 32, as used herein, can include a number of processors capable of executing instructions stored by the memory resource 33. Processing resource 32 can be integrated in a single device or distributed across multiple devices. The instructions e.g., computer-readable instructions (CRI)) can include instructions stored on the memory resource 33 and executable by the processing resource 32 for rendering a motion model of a heart 10. The computer system 20 is discussed further in relation to FIG. 5.

The computer system 20 is configured to control the signal generator 25 in accordance with predetermined strategies to selectively energize various pairs of surface electrodes. In operation, the computer system 20 is configured to obtain raw patch data (i.e., voltage readings) via the filter 27 and A-D converter 26 and use this raw patch data to determine the raw electrode location coordinates in three-dimensional space (X, Y. Z) of a catheter electrode positioned inside the heart 10 or chamber thereof (e.g., such as the roving electrode 17 mentioned above). In some embodiments, a phase of the patient's 11 cardiac cycle can be measured or otherwise determined when such electrode location coordinates are being received. For this purpose, in an embodiment, most or all of the conventional twelve (12) ECG leads, coupled to body surface electrodes and designated collectively by reference numeral 15, are provided to support the acquisition of an electrocardiogram (ECG) of the patient 11.

Alternatively, a reference electrode positioned in a fixed location in the heart 10, such as fixed reference electrode 31, may be used to provide a relatively stable signal that can be analyzed to determine the cardiac phase of the heart 10 in the cardiac cycle (e.g., placed at the coronary sinus). More generally, another catheter having an electrode, other than the moving or roving catheter, may be placed and maintained in a constant position relative to the heart 10 to obtain a relatively stable signal indicative of cardiac phase. As shown, the ECG leads 15 are coupled directly to the computer system 20 for acquisition and subsequent processing to obtain the phase of the heart 10 in the cardiac cycle. The ECG leads 15 may also be provided to other systems (not shown).

Note, the computer system 20 may employ filtering of the signals appearing on one or more of the ECG leads 15, which may introduce a predetermined amount of delay. For example, in an embodiment operating at 1200 samples/second, a 12-tap digital filter may be used with respect to the ECG-provided signals, which may have the effect of introducing a corresponding twelve time-step delay in the availability of the determined cardiac phase within computer system 20. In general, the relatively low latency in the availability of cardiac phase information may be deemed to have an immaterial impact on the accuracy of the generation of the cardiac mapping, and a subsequent "playback" of an animation of cardiac motion generated from the cardiac mapping.

In an example, cardiac mapping derived from localization data (e.g., NAVX™ data) can be damped and incorporate lag (e.g., as a result of filters). As such, motion of the catheter can be consistent with the animation of cardiac motion generated from the cardiac mapping. However, catheter motion may not be consistent with data generated through fluoroscopy and/or with a physiological motion of the heart 10, because of the incorporated lag.

Figure 2:
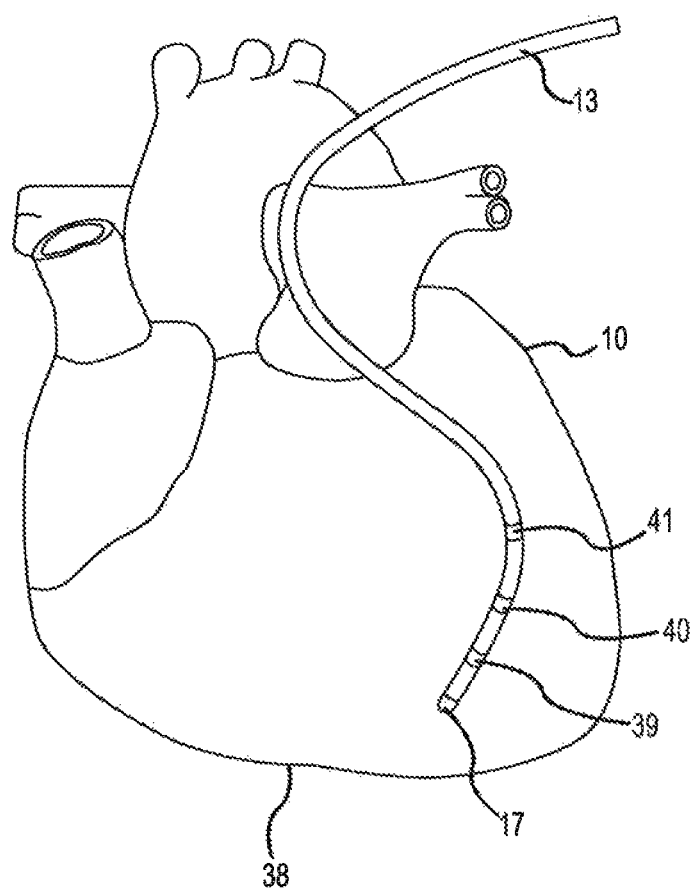
FIG. 2 illustrates a catheter with an electrode, in accordance with embodiments of the present disclosure.

FIG. 2 shows in greater detail an embodiment of the exemplary catheter 13 of FIG. 1. The catheter 13 may be a conventional EP catheter, as shown disposed only in the left ventricle 38 of the heart 10, for example. The EP catheter 13 may also include additional ring electrodes 39, 40 and 41, in addition to electrode 17, that collectively define the sensor. It should be understood that the catheter 13 may include still other electrodes, and in other embodiments such as in EP or RF ablation embodiments, the one or more other electrodes may be used for any number of diagnostic and/or therapeutic purposes. For instance, such electrodes and therefore such catheters may be used for performing ablation procedures, cardiac mapping, EP studies and other procedures. The invention is not limited to any one type of catheter or catheter-based system or procedure. In addition, as described above, the location sensor, in the described impedance-based localization embodiment, may comprise one or more of the catheter tip electrode and ring electrodes. All location information may be used to improve the determination of a location data point for use in rendering a motion model of the heart 10.

In some embodiments, the location data and cardiac phase data can be received as a motion sample associated with the cardiac wall motion during the cardiac cycle. In an example, the sensor (e.g., electrodes 17, 39, 40, 41) can be held against the cardiac wall at a particular location for a period of time to collect the location data, while the cardiac phase data is concurrently collected. Accordingly, as the cardiac wall moves, a number of points can be received that are representative of the cardiac wall motion. These points can be associated with the cardiac phase data, such that a position of the cardiac wall can be paired with a particular cardiac phase at which the location data was received.

In some examples, the sensor can be held at the particular location on the cardiac wall for a time period of 10 seconds, which may provide a sufficient motion sample associated with the cardiac wall motion. In particular, when using a cardiac mapping system, such as EnSite™ NavX™, the sensor can be held at the particular location for a time period of 10 to 15 seconds. When using a cardiac mapping system, such as MediGuide™, a satisfactory sample time period can be reduced to approximately 5 seconds. The duration of the sample time can span 1 or more respiratory cycles so that the data can be averaged (e.g., ensemble averaged) over this period. Given a sufficient algorithm, the time period can be reduced further to 1 to 3 cardiac cycles, which can be approximately 1 to 3 seconds. The EnSite™ Velocity™ and MediGuide™ cardiac mapping systems both incorporate respiration compensation algorithms, which can remove respiration artifact from the location data using signal filters.

In some embodiments, the location data and the cardiac phase data may generally not be collected at a uniform sample rate. When using an EnSite™ Velocity™ cardiac mapping system, a sample rate of the cardiac phase data can be 2 kilohertz, while a sample rate of the location data can be 98 hertz. To simplify processing, the cardiac phase data and the location data can be resampled to align the data to the sample rate. By resampling, the sample rate of the location data and the cardiac phase data can be matched such that the location data and cardiac phase data is time aligned. In an example, a time at which each location data point is collected can match a time at which each cardiac phase data point is taken.

Resampling can be done in several ways; the location data can be up-sampled to the higher rate of the cardiac phase data, or the cardiac phase data can be decimated down to the sample rate of the location data. Although either method is possible, up-sampling the location data to the cardiac phase data may not provide any benefit and may increase a computational load associated with the processing resource 32. In an example, the sample rate of the location data may be increased, but the information carried by it may not be increased because an interpolation step of filling in data to the higher sample rate only carries the information of the adjacent location data of the interpolation step.

In some embodiment, an ECG detection model can be used to determine time points of R-waves in a QRS complex of the cardiac cycle of the patient's 11 heart 10 from the cardiac phase data (e.g., ECG data). The following article, which is hereby incorporated by reference as though fully set forth herein, describes an ECG detection model in further detail:

Chesnokov, D. Individually adaptable Automatic QT Detector. *Computers in Cardiology.* 2006. 33:337-341.

In some embodiments, when a cardiac mapping system such as EnSite™ Velocity™ is used, the system can incorporate the ECG detection model. Determination of the time point of the R-wave in the QRS complex of the cardiac cycle allows for a cardiac phase to be assigned to each time point. In an example, phases can be assigned to each time point by uniform interpolation between neighboring R-waves to divide the cardiac cycle into incremental phases. In an example, the cardiac cycle can be divided into a number of incremental phases ranging from 10 to 100. For instance, the cardiac cycle can be divided into 10 phases (e.g., 10%, 20%, 30%, etc.), or the cardiac cycle can be divided into 100 phases (e.g., 1%, 2%, 3%, etc.). However, in some embodiments, the cardiac cycle can be divided into a number of incremental phases fewer than 10 or greater than 100.

The assigned phases can be a linear ramp function where the beginning of an R-wave is assigned a 0% phase and the next R-wave is assigned a 100% phase. R-waves are simultaneously assigned a 0% phase and a 100% phase, as these are equivalent in terms of cardiac position and the ECG.

In some embodiments, each location can be assigned a cardiac phase that has been determined through the ECG detection model. In an example, a time associated with the location data and the cardiac phase data can be used to assign the cardiac phase to the location data. The location data can then be assigned to the incremental phases. For example, where 10 incremental phases are chosen, a location can be assigned to one of the 10 incremental phases based on the cardiac phase associated with the location. Alternatively, where 100 incremental phases are chosen, the location can be assigned to one of the 100 incremental phases based on the cardiac phase associated with the location.

A greater number of incremental phases can result in a greater smoothness associated with transitions between geometries included in the motion model of the heart 10. For example, dividing a cardiac cycle into 10 discrete geometries associated with the heart 10 can result in a greater transition from one geometry to the next. Alternatively, dividing the cardiac cycle into 100 discrete geometries associated with the heart 10 can result in a smaller transition from one geometry to the next, thus creating a smoother transition from one geometry to the next. However, dividing the cardiac cycle into a greater number of incremental phases can result in fewer location data points in each incremental phase, which may affect an accuracy of the motion model.

In some embodiments, each incremental phase can include a range of cardiac phases. For example, where 10 incremental phases are chosen, such that incremental phases are divided into 10% increments, cardiac phases that fall between 5% below or 5% above a 20% incremental phase can be included in the 20% incremental phase. Alternatively, where 100 incremental phases are chosen, such that incremental phases are divided into 1% increments, cardiac phases that fall between 0.5% below or 0.5% above a 20% incremental phase can be included in the 20% incremental phase.

In some embodiments, multiple location data points may be included in each incremental phase. For example, where multiple location data points associated with cardiac phases fall in a range of cardiac phases associated with a particular incremental phase, multiple location data points can be included in the particular incremental phase. In addition, multiple location data points can be included in the particular incremental phase when location data points are collected over multiple cardiac cycles. For example, if location data is collected over 3 cardiac cycles, each incremental phase can include 3 location data points, one location data point from each cardiac cycle.

In some embodiments, an average of the location data points included in each incremental phase can be calculated. In some examples, an ensemble average can be used to calculate the average of the location data points included in each incremental phase. As a number of location data points received for each incremental phase increases, the average of the location data points can become more robust and lead to a greater accuracy associated with the motion model of the heart 10 created from the location data points.

In some embodiments, statistics can be calculated for the location data points included in each incremental phase. In an example, a standard deviation and/or a variance can be calculated for the location data points included in each incremental phase. The statistics can be used to determine a length of time necessary to collect motion samples by ensuring that an average position calculated from the location data points included in each incremental phase is reliable.

Figure 3A:
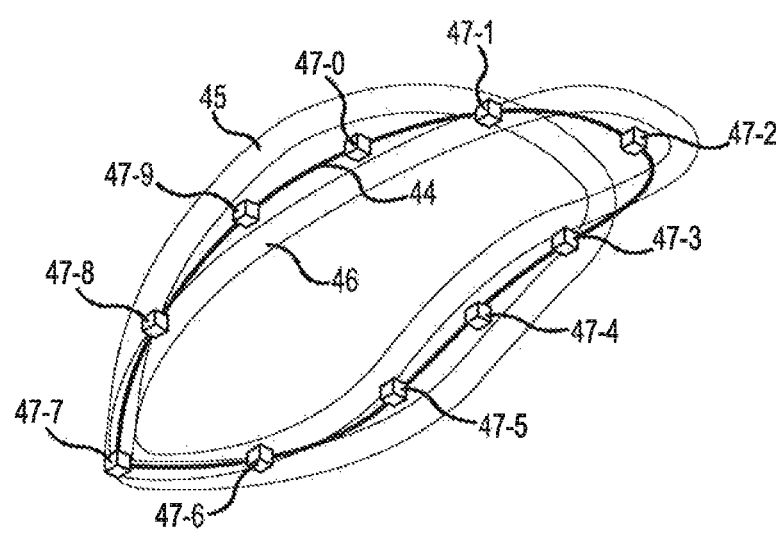
FIG. 3A illustrates motion samples and averaged motion samples associated with cardiac cycles, in accordance with embodiments of the present disclosure.

FIG. 3A illustrates motion samples and averaged motion samples associated with cardiac cycles, in accordance with embodiments of the present disclosure. A first motion sample 45 and second motion sample 46 associated with the cardiac wall motion, which can contain a number of data location points, can be received from the sensor attached to the catheter 13. In an example, the first motion sample 45 can contain location data points associated with a first cardiac cycle and the second motion sample 46 can contain location data points associated with a second cardiac cycle. As shown in FIG. 3A, a majority of the first motion sample 45 (e.g., location data points) does not overlap with the second motion sample 46. Average positions 47-0, 47-1, . . . , 47-9 can be calculated from the first motion sample 45 and the second motion sample 46 to create an averaged motion sample. Average positions 47-0, 47-1, . . . , 47-9 can each be associated with an incremental phase. For example, average position 47-0 can be associated with a 0% phase; average position 47-1 can be associated with a 10% phase; average position 47-2 can be associated with a 20% phase; average position 47-3 can be associated with a 30% phase; average position 47-4 can be associated with a 40% phase; average position 47-5 can be associated with a 50% phase; average position average position 47-6 can be associated with a 60% phase; average position 47-7 can be associated with a 70% phase; average position 47-8 can be associated with a 80% phase; and average position 47-9 can be associated with a 90% phase. In an example, an ensemble average motion sample can be obtained through the ensemble average of the first motion sample 45 and the second motion sample 46 and can include average positions 47-0, 47-1, . . . , 47-9.

In an example, incremental phases between approximately 70% and 80% can be associated with an end diastole phase of the heart 10, which can be used as a reference cardiac phase in embodiments of the present disclosure. In an example, the reference cardiac phase for purposes of the present disclosure can be computed as an offset from the QRS complex and can correspond to the incremental phases between approximately 70% to 80%. The cardiac cycle of the heart 10 can be defined by a current end diastole phase and a preceding end diastole phase and intermediate cardiac phases (e.g., 90% phase, 0% phase, 10% phase, 20% phase, 30% phase, 40% phase, 50% phase, 60% phase can be phases of the cardiac cycle between the end diastole phases. For example, the cardiac cycle of the heart can be defined as a period between QRS complexes (e.g., systole).

Figure 3B:
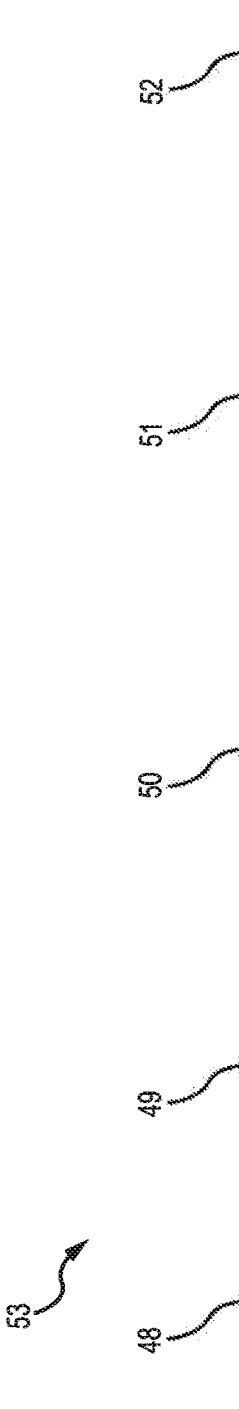
FIG. 3B illustrates a location data table, in accordance with embodiments of the present disclosure.

FIG. 3B illustrates a location data table, in accordance with embodiments of the present disclosure. The location data table 53 includes a time column that includes times T0 to T9, which correspond to phases 0% to 90% listed in the phase column 49. As illustrated, the location data table includes location data that has been assigned to 10 incremental phases ranging from a 0% cardiac phase to a 90% cardiac phase. A reference cardiac phase location can be defined for each phase in reference column 50. For example, the reference cardiac phase location P70 can correspond to a location data point (e.g., coordinates) associated with a phase of 70%, which corresponds to an end diastole phase of the cardiac cycle (e.g., reference cardiac phase). A cardiac phase location column 51 can include a location data point associated with each cardiac phase listed in phase column 49. For instance, cardiac phase location P0 can correspond to a location data point for a 0% phase, cardiac phase location P10 can correspond to a location data point for a 10% phase, etc. The cardiac phase location P70 can correspond to a location data point for a 70% phase, which can be the same location data point for the reference cardiac phase location.

A fiducial pair of coordinates can be determined for each of the incremental phases (e.g., 0%, 10%, 20%, etc.) based on the assigned location data for each phase. In an example, a cardiac phase offset can be determined for each phase. The cardiac phase offset can be a vector associated with a change in location between the reference cardiac phase location (e.g., end cardiac phase) and the intermediate cardiac phase location. For instance, the cardiac phase offset for the 70% phase is (0, 0, 0), as shown by the location data table 53, because the cardiac phase location at 70% phase (e.g., P70) is the same as the reference cardiac phase location (e.g., P70), since 70% is used as the reference cardiac phase location.

In some embodiments, a surface model of a heart 10 corresponding to the reference cardiac phase (e.g., diastolic position) can be received. In some embodiments, a catheter equipped with a position sensor can be inserted into the heart and can be moved within the heart to obtain a cloud of points. The cloud of points can be used to construct a surface model of the heart 10. In some embodiments, the surface model of the heart 10 can be obtained via an imaging system. For example, a segmented model can be derived from an imaging system. In some embodiments, the segmented model can be imported from an imaging system, such as, a computed tomography (CT) system, a magnetic resonance imaging (MRI) system, and/or an intra-cardiac echocardiography (ICE) system and can be registered using a mapping system, such as EnSite™ Fusion™. The segmented model can be fused and can be used as the surface model of the heart 10, acting as a reference geometry, much like the surface model constructed from the cloud of points. Because the surface model of the heart 10 is at the end cardiac phase, the cardiac phase location at the end cardiac phase (e.g., 70% phase) can be correlated to a position on the surface model of the heart 10. The cardiac phase offsets can be used to shift a coordinate of the surface model, such that the coordinate of the surface model changes for each phase, reflecting a motion of the heart 10. For example, a coordinate of the surface model constructed from the cloud of points and/or a coordinate of the surface model obtained from the CT and/or MRI can be shifted, thus reflecting the motion of the heart 10.

The fiducial pair of coordinates for each phase can include the reference cardiac phase location and the cardiac phase offset for each phase. In an example, a fiducial loop can contain a complete set of fiducial pairs over all phases. The fiducial pair of coordinates can be represented as:

$$\{L_{ref}, \Delta L_p\}$$

where $L_{ref}$ is an absolute location of the fiducial loop at the reference cardiac phase, and $\Delta L_p$ is the offset from the reference cardiac phase location at phase, p. Equivalently, the fiducial pair of coordinates can be represented using the following absolute pairs:

$$\{L_{ref}, L_p\}$$

where $L_{ref}$ is an absolute location of the fiducial loop at the reference cardiac phase, and $L_p$ is the absolute location of the fiducial loop at phase, p. In an example, use of offsets (e.g., $\Delta L_p$) can result in adding the offset to the coordinate of the surface model, whereas use of an absolute fiducial pairing can result in assigning a new coordinate to the coordinate of the surface model.

The fiducial loop can correspond to a particular point on the cardiac wall and can represent the motion of that point when the cardiac wall moves over the cardiac cycle. Fiducial loops can also be created for other points on the cardiac wall so coordinates of the surface model of the heart 10 can be shifted to create a motion model of the heart 10. Once the fiducial pairs for each fiducial loop are determined, the fiducial pairs can be used to determine the shift in coordinates from the surface model representing the reference cardiac phase (e.g., diastolic phase) to each particular cardiac phase. The shift in coordinates can be expressed as the following:

$$f: R_3 \rightarrow R_3$$

The shift in coordinates can be determined through function regression, in an example. For instance, function regression methods used in the EnSite™ Fusion™ module commercially available from St. Jude Medical, Inc., or as seen generally by reference to U.S. patent application Ser. No. 12/347,216, filed Dec. 31, 2008, hereby incorporated by reference as though fully set forth herein. Function regression methods can include use of a thin plate splines model, a radial basis networks model, and/or a mean value coordinates model.

In some examples, these function regression methods and/or other function regression methods can be employed. However, the method of thin plate splines can be preferred due to several factors including limitation of undue oscillations between fiducial points, maintenance of manifold surfaces in the shift in coordinates, and its straightforward implementation in software.

A summary of the thin plate splines model is shown below:

$$f(x) = Tx + \sum_{i=1}^{l} w_i g(x, x_i)$$

$$g(r) \begin{cases} c_0 r^{4-n} \ln(r), & (n = 2 \text{ or } n = 4) \\ c_1 r^{4-n}, & \text{otherwise} \end{cases}$$

$$g(r) \begin{cases} c_0 \ln(r), & (n = 4) \\ c_1 r, & (n = 3) \end{cases}$$

where the weights (w) are determined from a learning phase of the thin plate splines model. The following articles, which are hereby incorporated by reference as though fully set forth herein, describe the thin plate splines algorithm in further detail:

Bookstein, F L. Principal Warps: Thin Plate Splines and the Decomposition of Deformations. *IEEE Transactions on Pattern Analysis and Machine Intelligence*. 1989. 11:567-585.

Bookstein, F L. Thin-Plate Splines and the Atlas Problem for Biomedical Images. *Proceedings of the 12th International Conference on Information Processing in Medical Imaging*. July, 1991.

Once the shift in coordinates is computed for each phase, a current cardiac mapping can be determined from a current cardiac phase obtained from the ECG data. The current phase is obtained from the ECG data as previously discussed herein. In an example, R-waves are detected and the period between R-waves (e.g., defining the cardiac cycle) is computed. Because a cardiac phase at an instantaneous time point cannot be known until a following R-wave arrives, the period of the previous R-R interval is used to predict a current cardiac phase. If the period of the previous R-R interval is D, and a time from the last R-wave is d, then a current time point is assigned to the cardiac phase, as follows:

$$\text{phase} = \begin{cases} \left(\dfrac{d}{D}\right)*100\%, & d < D \\ 100\%, & d \geq \end{cases}$$

Accordingly, the current cardiac phase can be determined based on the previous cardiac phase. For example, the current cardiac phase can be determined based on a ratio between a time associated with a length of the previous cardiac cycle and a time since a current cardiac cycle began.

In some examples, if the following R-wave arrives later, relative to the previous R-R interval, then time points associated with intermediate cardiac phases occurring later in the cardiac cycle will each be assigned a 100% phase and appear as though they are end cardiac phases. This can cause motion of the cardiac motion model to pause, in an example. Alternatively, if the following R-wave arrives earlier relative to the previous R-R interval, then time points associated with intermediate cardiac phases occurring later in the cardiac cycle will never reach 100% phase and can immediately transition back to 0%. This can have the effect of causing the observed motion of the beating heart model to jump back to 0% abruptly.

Some embodiments of the present disclosure can include a recall mode and a real-time mode. In the recall mode, a number of cardiac cycles associated with the patient's 11 heart 10 can be recorded. Accordingly, an actual period of the R-R intervals associated with the cardiac cycles can be recorded and used later on to assign a cardiac phase for each of the R-R intervals. In the real-time mode, the period of the previous R-R interval can be used to predict a current cardiac phase associated with a current R-R interval, as discussed herein.

In a recall mode, where a user is operating in an offline review mode, as available in the EnSite™ Velocity™ cardiac mapping system, any issues caused by the following R-wave arriving earlier and/or later may not pose any issues, because the arrival of the following R-wave can be previously stored and can be utilized for an assignment of a cardiac phase for each particular RR interval. In real-time, alternative methods of determining the phase can be employed. For example, the value D can be determined as a minimum or a maximum for a number of prior cycles to avoid jumps or pauses in the motion model of the heart 10. In addition, in some examples, an average value of the R-R interval can be used to determine the value D to avoid jumps and/or pauses, although examples are not so limited.

In some embodiments, when the current phase (p) of the cardiac cycle is determined, a geometry of the heart chamber can be displayed based on the current cardiac phase of the cardiac cycle. If the current cardiac phase aligns with an incremental cardiac phase (e.g., 10% phase), a determination of the geometry of the heart chamber can be made by computing a regression function for that cardiac phase for each coordinate of the surface model of the heart 10. In an example, an offset approach can be used, where an offset is added to a coordinate of the surface model of the heart 10 to shift the coordinate and can be represented as:

$$\vec{x}_p = f_p(\vec{x}_{ref}) + \vec{x}_{ref}$$

Alternatively, an absolute approach can be used, where an absolute position of the coordinate of the surface model is defined and can be represented as:

$$\vec{x}_p = f_p(\vec{x}_{ref})$$

In some embodiments, where a current cardiac phase does not fall into one of the incremental cardiac phases (e.g., 10% phase) and thus an associated shift in coordinates for the incremental phase, the position of the coordinate of the surface model can be determined through interpolation. For example, where a current phase (e.g., 15%) is between two incremental cardiac phases (e.g., 10%, 20%), the coordinate associated with the current phase can be determined using an offset approach, as follows:

$$\vec{x}_p = (1-a)f_{p-}(\vec{x}_{ref}) + af_{p+}(\vec{x}_{ref}) + \vec{x}_{ref}$$

In a recall mode, each cardiac phase for which a shift in coordinates of the surface model has been determined can be pre-computed for each coordinate of the surface model and can be stored in a lookup table of phase geometries. Accordingly, instead of computing the function $f$ for each coordinate for which it is needed, the shift in coordinates of the surface model can be determined by referencing the lookup table of phase geometries. Accordingly, with the pre-computed lookup table of phase geometries, an interpolation may be the only operation that may need to be performed to determine the shift in coordinates of the surface model. Alternatively, a large number of phases (e.g., 100) can be pre-computed and included in the lookup table of phase geometries. As such, the interpolation step may be unnecessary. Alternatively, the shift in coordinates of the surface model can be computed as-needed for each coordinate of the surface model. For example, a geometry of the heart for each of the incremental phases can be computed in real-time, as opposed to being pre-computed and stored in a lookup table of phase geometries.

In some embodiments, the regression function can be a function of phase, as shown below:

$$f: R_4 \rightarrow R_3$$

The thin plate splines model can become a function of four variables, which are:

$$(x, y, z, p)$$

As such, the entire set of fiducial pairs in the fiducial loop can be used to create a single cardiac mapping instead of partitioning the fiducial pairs in the fiducial loop into groups according to cardiac phase in order to create a number of shifts in coordinates of the surface model, one for each of the number of partitioned phases.

Accordingly, during recall, interpolation between phases can now be implicit using an offset approach, as follows:

$$\vec{x}_p = f(\vec{x}_{ref}, p) + \vec{x}_{ref}$$

As discussed previously, numerous phases can be pre-computed for each coordinate of the surface model and stored in the lookup table of phase geometries. This can reduce a computational load associated with determining the shift in coordinates of the surface model.

Accordingly, a shift in coordinates of the surface model (e.g., geometry of the heart chamber) can be determined by correlating a cardiac phase with a phase geometry in the table of phase geometries. In some embodiments, a time can be associated with the phase geometry in the table of phase geometries, such that the shift in coordinates of the surface model can be determined by correlating the time with the phase geometry in the table of phase geometries. The table of phase geometries can provide a learned cardiac mapping of the heart 10 such that a geometry of the heart 10 at a particular phase and/or a particular time associated with the phase can be modeled. In some embodiments, an animation of a current cardiac cycle can be constructed by causing the phase geometry associated with each cardiac phase and/or time to be displayed in progression via display 23. For instance, the animation of the current cardiac cycle can be provided by shifting a coordinate of the surface model over each incremental phase of the cardiac cycle. In some embodiments, a number of vertices can form the surface model and can be shifted according to each incremental phase of the cardiac cycle to provide an animation of the cardiac cycle.

Figure 4:
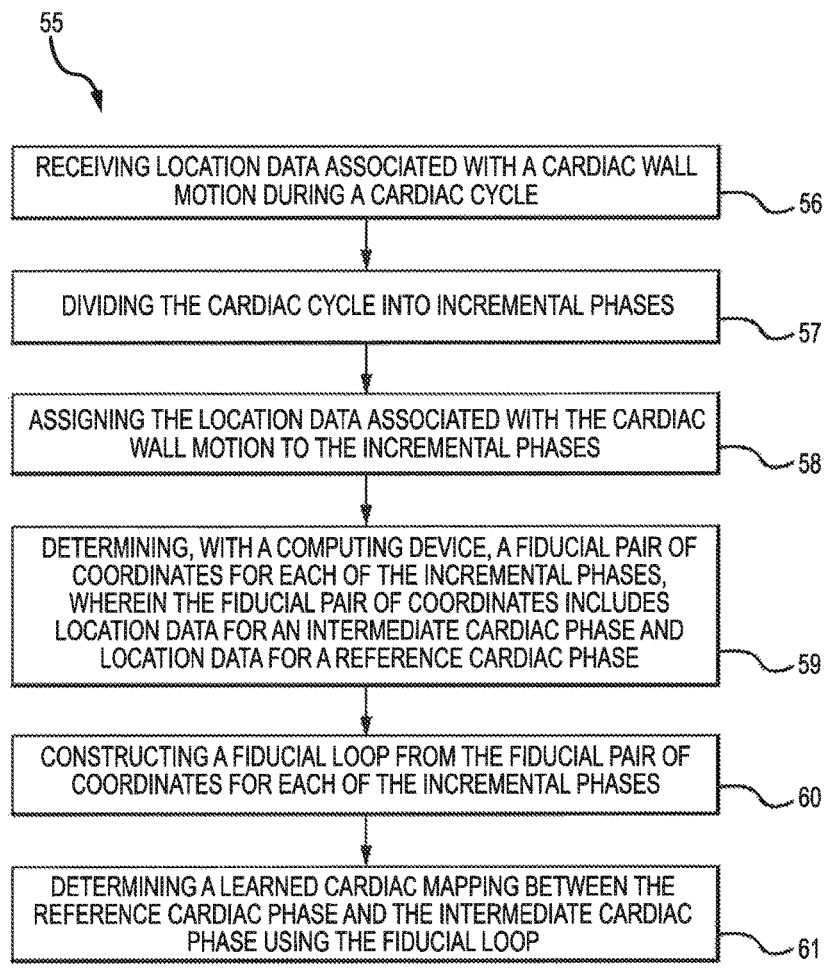
FIG. 4 illustrates a block diagram of an example of a method for rendering a motion model of a heart, in accordance with embodiments of the present disclosure.

FIG. 4 illustrates a block diagram of an example of a method for rendering a motion model of a heart, in accordance with embodiments of the present disclosure. In some embodiments, the method 55 can be executed by the computer system 20. The method 55 can include receiving location data associated with a cardiac wall motion during a cardiac cycle, at block 56. The location data can be received via an electrode 17 connected to a catheter 13 that is inserted into a patient's 11 heart 10. In some embodiments, cardiac phase data associated with the cardiac cycle can be received concurrently with the location data. The cardiac cycle of the heart 10 can be defined by a current reference cardiac phase and a preceding reference cardiac phase. In an example, the reference cardiac phases can be end diastole phases, such that the cardiac cycle is defined by a current end diastole phase and a preceding end diastole phase.

The cardiac cycle can further be defined by a number of intermediate cardiac phases that are between the current reference cardiac phase and the preceding reference cardiac phase. For example, as discussed herein, where the current reference cardiac phase is a current end diastole phase and the preceding reference cardiac phase is a preceding end diastole phase, an intermediate cardiac phase can be a systole phase.

In some embodiments, at block 57, the method 55 can include dividing the cardiac cycle into incremental phases. For example, the cardiac cycle can be divided into 1% phases, 2% phases, 5% phases, 10% phases, etc. The location data associated with the cardiac wall motion can be assigned to the incremental phases, at block 58. In an example, the location data associated with the cardiac wall motion can be assigned to one of the incremental phases based on a corresponding cardiac phase at which the location data was received. For instance, the location data can be associated with the particular cardiac phase at which it was received and can thereby be matched to one of the incremental phases.

The method 55 can include, at block 59, determining a fiducial pair of coordinates for each of the incremental phases. In an example, the fiducial pair of coordinates includes location data for an intermediate cardiac phase and location data for a reference cardiac phase. As such, the fiducial pair of coordinates can provide information associated with a change in position of the cardiac wall between the reference cardiac phase and the intermediate cardiac phase.

In some embodiments, the method 55, can include constructing a fiducial loop from the fiducial pair of coordinates for each of the incremental phases, at block 60. The fiducial loop can include a fiducial pair of coordinates for each of the incremental phases and can thus include information associated with a change in position of the cardiac wall throughout the cardiac cycle.

In some embodiments, a surface model of the heart 10 can be received that corresponds to the reference cardiac phase. In an example, each fiducial pair of coordinates in the fiducial loop can be used to determine a shift in a coordinate associated with the surface model of the heart 10. Accordingly, a learned cardiac mapping can be determined, at block 61, between the reference cardiac phase and the intermediate cardiac phase using the fiducial loop. The learned cardiac mapping can be used to determine a current cardiac mapping of the heart 10 based on a current cardiac phase. For example, the learned cardiac mapping can include a geometry of the heart 10 (e.g., shift in coordinates of the surface model) for cardiac phases and/or times associated with the cardiac phases.

In some embodiments, determining the learned cardiac mapping between the reference cardiac phase and the intermediate cardiac phase can include computing a lookup table of phase geometries. For example, as discussed herein, numerous cardiac phases and associated shifts in coordinates associated with the surface model of the heart 10 can be pre-computed and stored in the lookup table of phase geometries. A current cardiac phase and/or a time associated with the current cardiac phase can be used to determine an associated shift in a coordinate of the surface model through use of the lookup table of phase geometries. Accordingly, the coordinate associated with the surface model of the heart 10 can be shifted by correlating a current cardiac phase and/or a time associated with the cardiac phase with a phase geometry in the table of phase geometries.

In some embodiments, the current cardiac phase can be determined based on a previous cardiac phase. For example, the current cardiac phase can be determined based on a ratio between a time associated with a length of the previous cardiac cycle and a time since a current cardiac cycle began. For example, if a previous cardiac cycle was 1 second, and a time since the current cardiac cycle is 0.5 seconds, the ratio between the time associated with the length of the previous cardiac cycle and the time since the current cardiac cycle began can be 0.5, representing a 50% phase.

Figure 5:
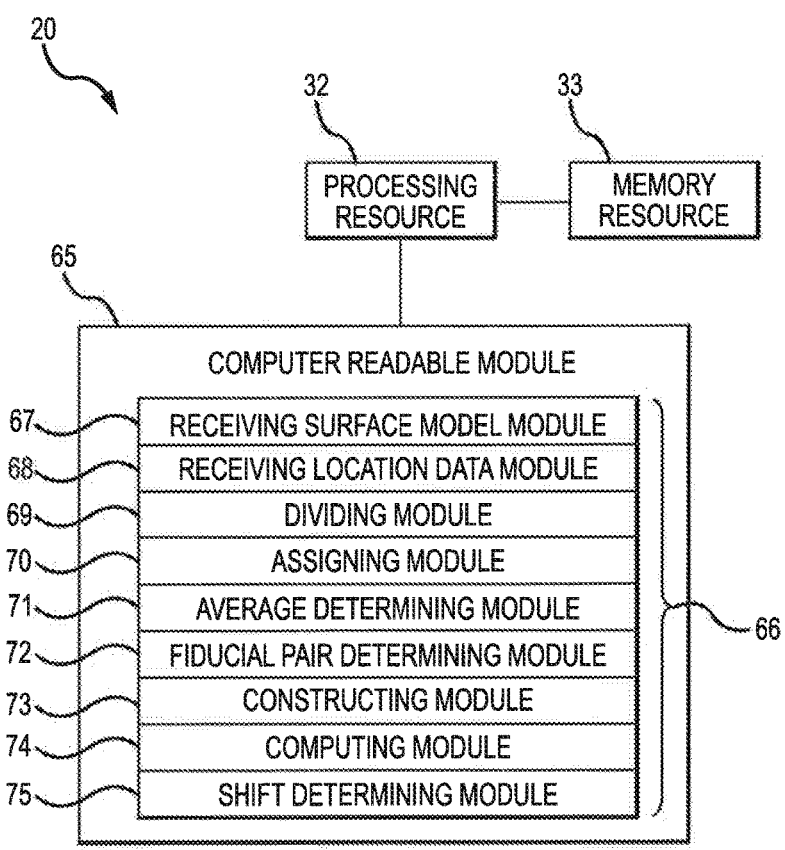
FIG. 5 illustrates a block diagram of an example of a computer-readable medium in communication with processing resources of a computing device, in accordance with embodiments of the present disclosure.

FIG. 5 illustrates a block diagram of an example of a computer-readable medium in communication with processing resources of a computing device, in accordance with embodiments of the present disclosure. The computer system 20, as discussed in relation to FIG. 1, can utilize software, hardware, firmware, and/or logic to perform a number of functions. The computer system 20 can include a number of remote computing devices.

The computer system 20 can be a combination of hardware and program instructions configured to perform a number of functions. The hardware, for example, can include one or more processing resources 32, computer readable medium (CRM) 65, etc. The program instructions (e.g., computer-readable instructions (CRI) 66) can include instructions stored on CRM 65 and executable by the processing resource 32 to implement a desired function (e.g., determine a fiducial pair of coordinates for each of the incremental phases from the averaged location data, etc.). The CRI 66 can also be stored in remote memory managed by a server and represent an installation package that can be downloaded, installed, and executed. The computer system 20 can include memory resources 33, and the processing resources 32 can be coupled to the memory resources 33.

Processing resources 32 can execute CRI 66 that can be stored on an internal or external non-transitory CRM 65. The processing resources 32 can execute CRI 66 to perform various functions, including the functions described with respect to FIG. 1 to FIG. 4.

A number of modules 67, 68, 69, 70, 71, 72, 73 can be sub-modules or other modules. For example, the dividing module 67 and the assigning module 68 can be sub-modules and/or contained within a single module. Furthermore, the number of modules 67, 68, 69, 70, 71, 72, 73 can comprise individual modules separate and distinct from one another.

A receiving surface model module 67 can comprise CRI 66 and can be executed by the processing resource 32 to receive a surface model of the heart 10 corresponding to an end diastole phase of a cardiac cycle. The surface model of the heart 10 can be formed from location data received from the electrode 17 and can correspond to a reference cardiac phase (e.g., end diastole phase). Alternatively, the surface model of the heart 10 can be generated at a previous time and received via the computer system 20.

A receiving location data module 68 can comprise CRI 66 and can be executed by the processing resource 32 to receive location data associated with a cardiac wall motion during the cardiac cycle. As discussed herein, the location data can be received from the electrode 17 connected to the catheter 13, which is inserted into the heart 10. In an example, the electrode 17 can be held against a wall of the heart 10 for at least one cardiac cycle.

A dividing module 69 can comprise CRI 66 and can be executed by the processing resource 32 to divide the cardiac cycle into incremental phases. In some examples, the cardiac cycle can be divided into a range of phases between 10 phases and 100 phases. For instance, the cardiac cycle can be divided into a 10% phase, 20% phase, 30% phase, etc. Alternatively, the cardiac cycle can be divided into a 1% phase, 2% phase, 3% phase, etc.

An assigning module 70 can comprise CRI 66 and can be executed by the processing resource 32 to assign the location data associated with the cardiac wall motion to the incremental phases based on corresponding cardiac phase associated with the location data. For example, where the cardiac cycle is divided into 100 phases, location data associated with a 1% cardiac phase can be assigned to the 1% incremental cardiac phase and location data associated with a 75% cardiac phase can be assigned to the 75% incremental cardiac phase.

An average determining module 71 can comprise CRI 66 and can be executed by the processing resource 32 to determine an average of the location data assigned to each of the incremental phases. In an example, where location data associated with multiple locations is included in one of the incremental phases, an average of the data can be taken such that one average location data point can be determined. As discussed herein, in some examples, an ensemble average of the location data can be taken.

A fiducial pair determining module 72 can comprise CRI 66 and can be executed by the processing resource 32 to determine a fiducial pair of coordinates for each of the incremental phases from the averaged location data. In some examples, the fiducial pair of coordinates for each phase can include the reference cardiac phase location and the cardiac phase offset for each phase. Accordingly, the fiducial pair of coordinates for each phase can provide information associated with a motion of the cardiac wall of the heart 10. In some embodiments, the fiducial pair of coordinates can be interpolated in response to the fiducial pair of coordinates being associated with a cardiac phase that is between incremental phases. For example, where fiducial pairs have been determined for a 10% phase and a 20% phase, a fiducial pair can be interpolated for a 17% phase.

In some embodiments, the fiducial pair of coordinates can be an offset from a coordinate associated with the surface model of the heart 10. For example, the fiducial pair of offset coordinates can be used to shift a coordinate of the surface model to a position indicated by the offset. Alternatively, the fiducial pair of coordinates can be an absolute location of the coordinate associated with the surface model of the heart 10. For example, the fiducial pair of absolute coordinates can define a shifted position of the surface model of the heart 10.

A constructing module 73 can comprise CRI 66 and can be executed by the processing resource 32 to construct a fiducial loop from the fiducial pair of coordinates for each of the incremental phases. In an example, the fiducial loop can include a fiducial pair of coordinates for each of the incremental phases and can thus include information associated with a change in position of the cardiac wall throughout the cardiac cycle. In an example, each fiducial pair of coordinates in the fiducial loop can be used to determine a shift in a coordinate associated with the surface model of the heart 10.

A computing module 74 can comprise CRI 66 and can be executed by the processing resource 32 to compute a lookup table of phase geometries based on the fiducial loop. In an example, the lookup table can include a shift in coordinates of the surface model and an associated cardiac phase of the cardiac cycle and/or associated time. Accordingly, the lookup table can be used to determine a geometry of the heart 10 to display based on the current cardiac phase of the current cardiac cycle and/or a time associated with the current cardiac phase of the current cardiac cycle.

A shift determining module 75 can comprise CRI 66 and can be executed by the processing resource 32 to determine a shift in coordinates of the surface model based on the lookup table and a current cardiac phase of the cardiac cycle. In an example, the coordinates of the surface model can be shifted with a progression of the cardiac phase such that the surface model reflects a geometry of the heart 10 associated with a current cardiac phase. For instance, a determination of the shift in coordinates of the surface model can be made by using the current cardiac phase and/or time associated with the current cardiac phase to look up the shift in coordinates in the lookup table. In some embodiments, an animation of a change in the geometry of the heart 10 during the cardiac cycle can be determined based on the current cardiac phase of the cardiac cycle using the lookup table. The animation of the change in geometry can be displayed via display 23.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for determination of a cardiac mapping and rendering a motion model of a beating heart has been described above with a certain degree of particularity, those skilled in the art could make numerous alterations to the disclosed embodiments without departing from the spirit or scope of this disclosure. All directional references upper, lower, upward, downward, left, right, leftward, rightward, top, bottom, above, below, vertical, horizontal, clockwise, and counterclockwise only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of rendering a motion model of a heart, the method comprising:
   receiving location data associated with a cardiac wall motion during a cardiac cycle;
   dividing the cardiac cycle into incremental phases;
   assigning the location data associated with the cardiac wall motion to the incremental phases;
   determining, with a computing device, a fiducial pair of coordinates for each of the incremental phases, wherein the fiducial pair of coordinates includes location data for an intermediate cardiac phase and location data for a reference cardiac phase;
   constructing a fiducial loop from the fiducial pair of coordinates for each of the incremental phases;
   determining a learned cardiac mapping between the reference cardiac phase and the intermediate cardiac phase using the fiducial loop;
   receiving a surface model of the heart; and
   shifting a coordinate associated with the surface model according to the learned cardiac mapping.

2. The method of claim 1, wherein determining the learned cardiac mapping between the reference cardiac phase and the intermediate cardiac phase includes computing a lookup table of phase geometries.

3. The method of claim 2, wherein the surface model of the heart corresponds to the reference cardiac phase.

4. The method of claim 3, further comprising shifting the coordinate associated with the surface model of the heart using the lookup table of phase geometries.

5. The method of claim 4, wherein shifting the coordinate associated with the surface model of the heart is determined by correlating a cardiac phase with a phase geometry in the table of phase geometries.

6. The method of claim 1, wherein determining the learned cardiac mapping between the referenced cardiac phase and the intermediate cardiac phase includes computing a geometry of the heart for at least one of the incremental phases.

7. The method of claim 1, further comprising determining a current cardiac mapping using the learned cardiac mapping and a current cardiac phase.

8. The method of claim 7, wherein the current cardiac phase is determined based on a previous cardiac phase.

9. The method of claim 7, wherein the current cardiac phase is determined based on a ratio between a time associated with a length of the previous cardiac cycle and a time since a current cardiac cycle began.

10. A non-transitory computer-readable medium storing instructions for rendering a motion model of a heart, the instructions executable by a machine to cause the machine to:
    receive a surface model of the heart corresponding to an end diastole portion of a cardiac cycle;
    receive location data associated with a cardiac wall motion during the cardiac cycle;
    divide the cardiac cycle into incremental phases;
    assign the location data associated with the cardiac wall motion to the incremental phases based on corresponding cardiac phase data associated with the location data;
    determine an average of the location data assigned to each of the incremental phases;
    determine a fiducial pair of coordinates for each of the incremental phases from the averaged location data;
    construct a fiducial loop from the fiducial pair of coordinates for each of the incremental phases;
    compute a lookup table of phase geometries based on the fiducial loop; and
    determine a shift in coordinates of the surface model based on the lookup table and a current cardiac phase of the cardiac cycle.

11. The computer-readable medium of claim 10, further comprising instructions executable to display a geometry of the heart based on the current cardiac phase of the cardiac cycle using the lookup table.

12. The computer-readable medium of claim 11, further comprising instructions executable to display an animation of a change in the geometry of the heart during the cardiac cycle based on the current cardiac phase of the cardiac cycle using the lookup table.

13. The computer-readable medium of claim 10, wherein the instructions executable to receive a surface model of the heart include instructions executable to receive a segmented model derived from an imaging system.

14. The computer-readable medium of claim 10, further comprising instructions executable to interpolate the fiducial pair of coordinates in response to the current cardiac phase being between adjacent incremental phases.

15. The computer-readable medium of claim 10, wherein the fiducial pair of coordinates is an offset from a coordinate associated with the surface model of the heart.

16. The computer-readable medium of claim 10, wherein the fiducial pair of coordinates is an absolute location of the coordinate associated with the surface model of the heart.

17. A system for rendering a motion model of a heart, comprising:
   a computing device comprising processor resources and memory resources, the memory resources storing computer-readable instructions that, when executed by the processor resources, cause the processor resources to:
   receive a motion sample associated with a cardiac wall motion during a cardiac cycle from a sensor operatively connected to a catheter, wherein the motion sample contains location data associated with the cardiac wall motion and cardiac phase data associated with the location data;
   divide the cardiac cycle into incremental phases;
   assign the location data to the incremental phases based on the corresponding cardiac phase data;
   determine a fiducial pair of coordinates for each of the incremental phases based on the assigned location data;
   construct a fiducial loop from the fiducial pair of coordinates for each of the incremental phases;
   determine a learned cardiac mapping for the cardiac cycle that includes a lookup table of phase geometries; and
   display an animation of a current cardiac cycle based on the lookup table of phase geometries and a current cardiac phase by shifting a coordinate associated with a received surface model according to the lookup table of phase geometries.

18. The system of claim 17, wherein the fiducial pair of coordinates includes location data for an intermediate cardiac phase and location data for an end cardiac phase.

19. The system of claim 17, further comprising instructions executable by the processor resources to:
   receive a surface model of a heart corresponding to the end cardiac phase; and
   shift a coordinate of the surface model through use of the lookup table of phase geometries and the current cardiac phase.

20. The system of claim 19, wherein the animation of the current cardiac cycle is provided by shifting the coordinate of the surface model over each incremental phase of the cardiac cycle.

* * * * *